US012109311B2

(12) United States Patent
Slocum et al.

(10) Patent No.: US 12,109,311 B2
(45) Date of Patent: Oct. 8, 2024

(54) LYOPHILIZATION SYSTEMS AND METHODS

(71) Applicant: Massachusetts Institute of Technology, Cambridge, MA (US)

(72) Inventors: Alexander H. Slocum, Bow, NH (US); Bernhardt Levy Trout, Lexington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 657 days.

(21) Appl. No.: 17/359,394

(22) Filed: Jun. 25, 2021

(65) Prior Publication Data

US 2022/0062180 A1 Mar. 3, 2022

Related U.S. Application Data

(60) Provisional application No. 63/072,633, filed on Aug. 31, 2020.

(51) Int. Cl.
*A61K 9/19* (2006.01)
*F26B 5/06* (2006.01)
*H02N 15/00* (2006.01)

(52) U.S. Cl.
CPC .................. *A61K 9/19* (2013.01); *F26B 5/06* (2013.01); *H02N 15/00* (2013.01)

(58) Field of Classification Search
CPC .............. F26B 5/06; A61K 9/19; H02N 15/00
USPC .......................................................... 34/296
See application file for complete search history.

(56) References Cited

U.S. PATENT DOCUMENTS

| 3,192,645 | A | | 7/1965 | Georg-Wilhelm et al. |
| 3,397,462 | A | * | 8/1968 | Jellicich ..................... F26B 5/06 |
| | | | | 34/92 |
| 5,154,007 | A | * | 10/1992 | Piunno ...................... F26B 5/04 |
| | | | | 34/302 |
| 5,515,618 | A | | 5/1996 | Matsumura et al. |
| 5,964,043 | A | | 10/1999 | Oughton et al. |
| 6,005,281 | A | | 12/1999 | Conboy et al. |
| 6,297,479 | B1 | | 10/2001 | Wefers |

(Continued)

FOREIGN PATENT DOCUMENTS

| CN | 109715846 A | | 5/2019 | |
| CN | 109791019 A | * | 5/2019 | ............... A61L 2/04 |

(Continued)

OTHER PUBLICATIONS

International Search Report and Written Opinion mailed Oct. 19, 2021, for Application No. PCT/US2021/039241.

(Continued)

*Primary Examiner* — Stephen M Gravini
(74) *Attorney, Agent, or Firm* — Wolf, Greenfield & Sacks, P.C.

(57) ABSTRACT

System and methods related to lyophilization of pharmaceutical products are disclosed. In some embodiments, vials of product are moved through a system using one or more movers which are electromagnetically levitated and moved through the system without making mechanical contact with each other or the system. Load lock chambers may allow a mover to enter from one process region's environment and then be brought to an environment condition of the next process region to allow materials to be passed through conditioning, nucleation, and/or vacuum drying regions prior to finally exit the system to an unloading zone. The movers may then be cleaned or reloaded with vials to begin the process again with a new load of vials.

20 Claims, 5 Drawing Sheets

(56) References Cited

U.S. PATENT DOCUMENTS

| | | | |
|---|---|---|---|
| 9,796,273 B2 * | 10/2017 | Ragazzini | B60M 7/00 |
| 9,942,950 B2 * | 4/2018 | Zickel | H05B 6/688 |
| 10,710,821 B2 * | 7/2020 | Beppu | F26B 5/06 |
| 10,865,131 B2 * | 12/2020 | Ekstrand | C02F 11/13 |
| 11,047,620 B2 * | 6/2021 | Beutler | F26B 21/003 |
| 11,090,711 B2 * | 8/2021 | Golfetto | B01D 3/00 |
| 11,185,087 B2 * | 11/2021 | Nguyen | A23F 5/405 |
| 11,448,463 B2 * | 9/2022 | Ganguly | F26B 5/06 |
| 11,867,461 B2 * | 1/2024 | Kozlowski | F26B 5/06 |
| 11,969,452 B2 * | 4/2024 | Ruggiero | A61P 39/00 |
| 2011/0113644 A1 | 5/2011 | Itou et al. | |
| 2015/0128445 A1 | 5/2015 | Dittrich et al. | |
| 2020/0030995 A1 | 1/2020 | Lu et al. | |
| 2020/0062516 A1 | 2/2020 | Beppu et al. | |
| 2020/0158431 A1 | 5/2020 | Trout et al. | |
| 2020/0248963 A1 | 8/2020 | Beutler et al. | |
| 2022/0062180 A1 * | 3/2022 | Slocum | F26B 5/042 |

FOREIGN PATENT DOCUMENTS

| | | |
|---|---|---|
| DE | 2262252 A1 | 7/1973 |
| DE | 102019106261 A1 | 4/2020 |
| EP | 2420450 A1 | 2/2012 |
| EP | 3231747 B1 | 10/2017 |
| EP | 3392584 A1 * | 10/2018 ............ F26B 21/003 |
| EP | 3590874 A1 | 1/2020 |
| JP | S60-191177 A | 9/1985 |
| JP | H02-126089 A | 5/1990 |
| JP | 7186718 B2 * | 12/2022 ............ F26B 21/003 |
| WO | 96/03289 A1 | 2/1996 |
| WO | WO-2014024044 A1 * | 2/2014 ............ G01R 27/04 |
| WO | WO 2014/053449 A2 | 4/2014 |
| WO | WO 2017/178246 A2 | 10/2017 |
| WO | WO-2018055758 A1 * | 3/2018 ............... A61L 2/04 |
| WO | WO-2022046273 A1 * | 3/2022 ............... A61K 9/19 |

OTHER PUBLICATIONS

Pisano et al., Achieving continuous manufacturing in lyophilization: Technologies and approaches. Eur J Pharm Biopharm. Sep. 2019;142:265-279. doi: 10.1016/j.ejpb.2019.06.027 Epub Jun. 25, 2019.

Extended European Search Report mailed Aug. 20, 2024, for Application No. EP21862293.4.

* cited by examiner

LYOPHILIZATION SYSTEMS AND METHODS

CROSS-REFERENCE TO RELATED APPLICATIONS

This Application claims the benefit under 35 U.S.C. § 119(e) of U.S. Provisional Application Ser. No. 63/072,633, filed on Aug. 31, 2020, which is incorporated herein in its entirety.

STATEMENT REGARDING FEDERALLY FUNDED RESEARCH

This disclosure was made with Government support under Grant No. U01 FD006755 awarded by the Food and Drug Administration. The Government has certain rights in the disclosure.

FIELD

Disclosed embodiments are related to systems and methods for lyophilization of pharmaceuticals.

BACKGROUND

Many therapeutic compositions (i.e., "drugs") have an aqueous form and may be refrigerated. This may include therapeutic compositions such as testosterone, various biologics including monoclonal antibodies (mAbs), vaccines, gene therapy, cell therapy products, exosomes, and any number of other appropriate types of therapeutic compositions. However, if these therapeutic compositions can be freeze dried without adversely affecting their molecular structure, they can be transported at room temperature and then reconstituted before use. This can greatly save costs, and in the case of vaccines, can be a critical factor when combating disease in order to rapidly immunize a population.

SUMMARY

In some embodiments, a system for lyophilization of a therapeutic composition may be configured such that containers of product are carried on movers which are electromagnetically levitated and moved through the system without making mechanical contact with each other or the machine, where load lock chambers with sealable entrance and exit doors allow a mover to enter from one process region's environment and then be brought to the environment condition of the next process region until the movers have moved from an initial atmospheric region where containers loaded on the movers move through conditioning, nucleation, and vacuum drying regions to finally exit the system to an unloading zone. The movers can then be cleaned or reloaded with containers to begin the process again with a new load of containers. Within the drying region, independently controllable radiant heaters may enable thermal energy input control to the movers based on sensors that can sense the state of the product as it is being dried.

In one embodiment, a system for lyophilization of pharmaceutical products includes: at least one mover configured to support one or more containers containing a therapeutic composition; an inlet of the system for receiving the at least one mover; an outlet of the system for outputting the at least one mover from the system; and a plurality of chambers disposed between the inlet and outlet. The plurality of chambers may include at least a first chamber configured to perform a nucleation operation on the therapeutic composition and a second chamber disposed downstream of the first chamber configured to perform a vacuum drying operation on the therapeutic composition. Additionally, the system for lyophilization may also include a plurality of stators configured to electromagnetically levitate and move the at least one mover from the inlet, through the plurality of chambers, and to the outlet.

In one embodiment, a method of lyophilizing a therapeutic composition includes: electromagnetically levitating at least one container including the therapeutic composition; electromagnetically moving the at least one container into a first chamber; performing a nucleation operation on the therapeutic composition in the first chamber; electromagnetically moving the at least one container from the first chamber to a second chamber; performing a vacuum drying operation on the therapeutic composition in the second chamber; and electromagnetically moving the at least one container from the second chamber to an outlet.

In one embodiment, a system for lyophilization of pharmaceutical products includes at least one mover configured to support one or more containers containing a therapeutic composition; an inlet of the system for receiving the at least one mover; an outlet of the system for outputting the at least one mover from the system; at least one load lock chamber disposed between the inlet and outlet; at least one process chamber disposed downstream of the load lock chamber; a plurality of stators configured to electromagnetically levitate and move the at least one mover from the inlet, through the at least one load lock chamber and the at least one process chamber to the outlet; at least one processor configured to control the stators, the at least one load lock chamber, and the at least one process chamber.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings.

Figure 1:
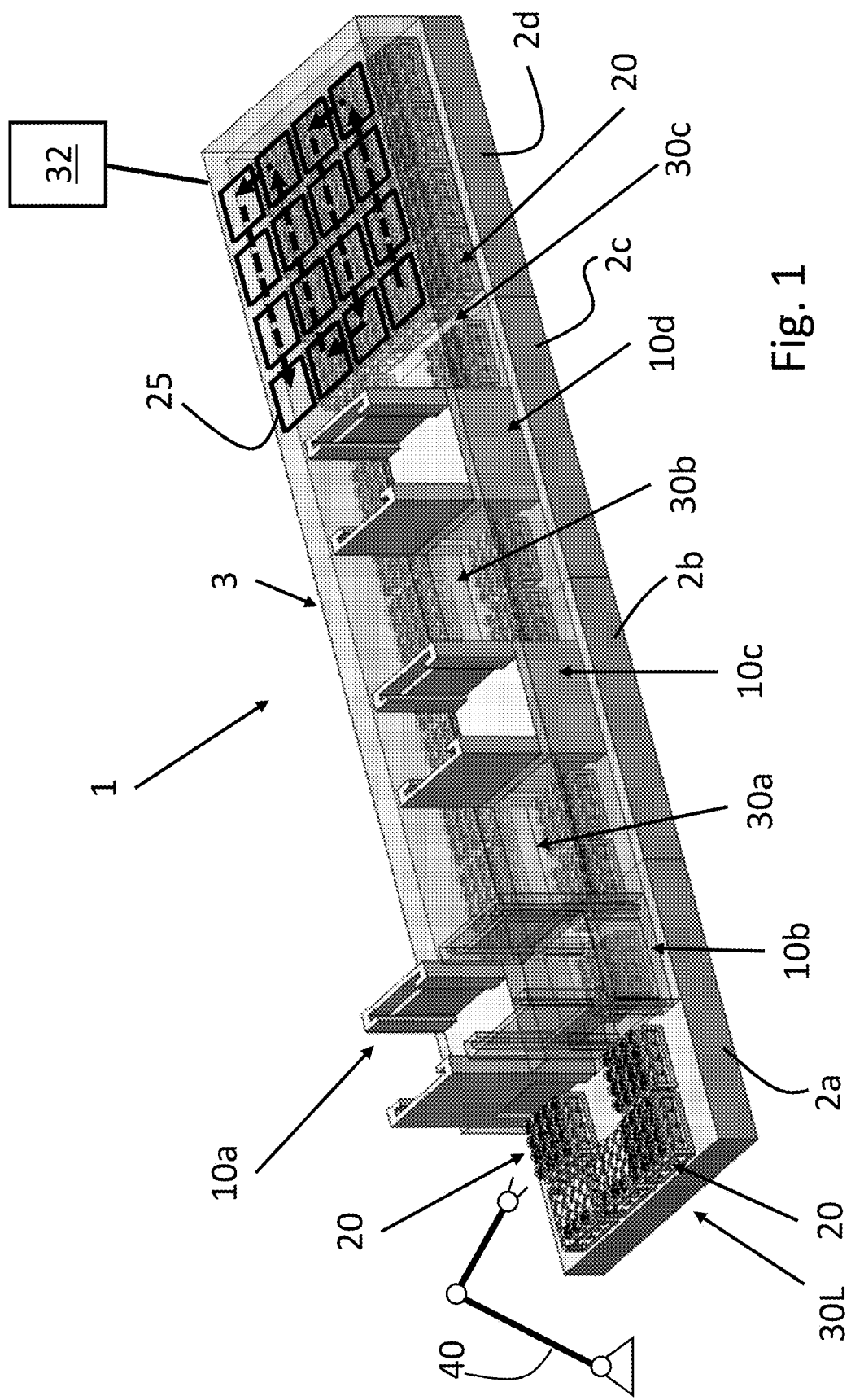
FIG. 1 is an isometric view of a lyophilization system according to one embodiment.

In the drawings, preferred embodiments of the disclosure are illustrated by way of example, it being expressly understood that the description and drawings are only for the purpose of illustration and preferred designs and are not intended as a definition of the limits of the disclosure.

DETAILED DESCRIPTION

Typical lyophilization systems predominantly process containers, such as vials holding a therapeutic composition, in a batch mode, where large trays of containers are loaded into one or more chambers and then processed. For example, the containers may be freeze-dried in batches. Batch freeze-drying may comprise three stages: (a) freezing the liquid solution in a container, (b) drying the material by removing water via sublimation under vacuum, and (c) removing residual moisture via desorption under vacuum.

Due to the nonuniform nature of such chambers, one or more process parameters may vary across the chamber volume, which may contain tens of thousands of containers. In addition, as trays of vials are slid around to load the chambers or moved between chambers, the vials may be exposed to mechanical shocks and/or other movements, which may affect the contents of the containers as they are being processed as part of the lyophilization process. In addition, particles may be generated from sliding contact motions that may contaminate product in vials. These and other disturbances and variances may be random in nature and unpredictable. Accordingly, such a random process may lead to random results for the final (processed) product, which may lead to low effective throughputs, and correspondingly high costs, to obtain a final acceptable product.

Some improvements over conventional batch lyophilization systems have been proposed, including spraying frozen pharmaceutical materials onto a belt or mechanical conveying of trays of vials. However, this mechanical conveyance creates the possibility of random shocks and other effects that may affect one or more molecules of a therapeutic composition. In addition, mechanical conveying introduces the chance of undesirable particle contamination due to wear of the mechanical components of the conveyance system. Furthermore, for the long drying times where ice crystals sublimate, many trays of vials are still treated essentially as a batch operation.

In view of the above, the Inventors have recognized a need for lyophilization systems capable of providing improved control of the lyophilization process for either discrete batches and/or continuous production of therapeutic composition moving through a system in some embodiments. Additionally, avoiding undesired mechanical shocks, random vibrations, and particulate contamination may also be desirable in some embodiments. Accordingly, the Inventors have recognized the benefits associated with lyophilization systems that use at least one mover, and in some instances a plurality of movers, where each mover is configured to support at least one container including a therapeutic composition disposed therein. The one or more movers may be configured to be magnetically levitated and moved through a plurality of chambers that perform various operations on the therapeutic composition as the one or more movers are magnetically moved from an inlet of the system through the chambers of the system to a corresponding outlet of the system.

In some embodiments, a lyophilization system may include at least one mover, and in some instances a plurality of movers, that are configured to support one or more containers containing a therapeutic composition disposed therein on each mover. The system may include an inlet that movers may be inserted into and a corresponding outlet for outputting the at least one mover from the system. A plurality of chambers may be disposed between the inlet and the outlet of the system for performing a variety of different operations on the therapeutic composition. The plurality of chambers may include at least first and second chambers that are configured to perform a nucleation operation (e.g., arranging ions, atoms, and/or molecules of the therapeutic compound in a pattern characteristic of a crystalline solid) and a vacuum drying operation on the therapeutic composition. In some embodiments, the second chamber used to perform the vacuum drying operation may be located downstream from the first chamber used to perform the nucleation operation. In some embodiments, the at least one mover is electromagnetically levitated. In order to electromagnetically levitate and move the at least one mover through the system, a lyophilization system may include a plurality of stators disposed in a pattern on a surface over which the movers may be levitated. In some embodiments, a processor may control a flow of current supplied to the different stators using feedback from associated sensors that are configured to interact with the at least one mover located above the stator to electromagnetically (magnetically) levitate and control the motion of the movers from the inlet through the plurality of chambers to the outlet. In some embodiments, the stators may be configured such that the movement of each of the movers through the lyophilization system may be controlled independently.

As noted above, a lyophilization system may include any number of different processing chambers disposed between an inlet and an outlet of the system. For example, in some embodiments, a lyophilization system may include a third chamber that is disposed upstream from a chamber used to perform a nucleation operation on a therapeutic composition disposed in one or more containers and supported by an associated mover (e.g., the first chamber as described herein). In some embodiments, this third chamber may be a conditioning chamber that includes appropriate temperature control systems, such as a cryogenic cooling system, that may pre-cool the therapeutic composition to a desired temperature prior to moving the therapeutic composition into the nucleation chamber. In some instances, the therapeutic composition may be cooled to a temperature below a freezing temperature of a liquid in which the therapeutic composition is disposed such that the liquid is supercooled.

As noted above, in some embodiments, it may be desirable to avoid unnecessary shocks and vibrations applied to a therapeutic composition during a lyophilization process. Accordingly, in some embodiments, the systems described herein may have a substantially continuous surface that extends from the inlet of a system through the plurality of downstream chambers to a corresponding outlet of the system. While in some instances, a substantially continuous surface may be a substantially continuous flat level surface relative to a local direction of gravity, in some embodiments, the surface may have some adjacent portions where minor discontinuities in height between the adjacent portions of the surface may be present. However, a change in hover height of a mover over adjacent portions of a surface, and the corresponding stators, may change by less than 20% of a predetermined hover height variance over a width of the mover. Thus, the one or more movers of the lyophilization system may be magnetically levitated and moved over the substantially continuous surface through the plurality of chambers of the system with substantially fewer vibrations and shocks than may be experienced using mechanical conveyances and/or manual operations. Again this may enable the production of a more uniform product with more uniform processing histories and corresponding properties.

In order to provide appropriate processing conditions within each of the various chambers of a lyophilization system, it may be desirable to use a plurality of load lock chambers that may be used to isolate the atmospheres within each processing chamber. For example, load lock chambers may be disposed between an inlet of the system and a first upstream chamber, between adjacent chambers, and between a final chamber and an outlet of the system. Each load lock chamber may include an appropriate upstream and downstream door that may be selectively opened and closed (sealed) to permit a mover to enter or exit. For example, an upstream door may be opened to permit a mover and the corresponding containers, including a therapeutic composition disposed therein, to be moved into the load lock chamber from an upstream opening or processing chamber and sealed therein. The upstream door may then be closed, and an atmosphere within the load lock chamber may then be appropriately controlled to provide a desired pressure, temperature, and/or composition prior to opening the downstream door. The mover may then be electromagnetically moved into the next downstream processing chamber and/or outlet after which the downstream door of the load lock chamber may be closed. Of course, while the use of load lock chambers is described herein, it should be understood that any appropriate method of transferring movers and the associated containers supported thereon between chambers may be used, as the disclosure is not limited to any particular method and/or construction. Any system that can allow a mover to electromagnetically move from one environment to another may be used, including but not limited to the discrete load lock type system described herein and alternatively or in addition, a revolving door type system may be used.

As noted above, it is common for temperature differentials to be present within a chamber used for freeze-drying operations and/or for a therapeutic composition contained on one mover to sublimate differently than a therapeutic composition on a separate mover. Accordingly, it may be desirable in some embodiments to independently control the temperatures of different volumes of therapeutic composition contained in containers supported on different movers disposed within a freeze-drying chamber. In such an embodiment, a system may include a plurality of radiant heaters that are directed towards different regions of a freeze-drying chamber. In some embodiments, these radiant heaters may be disposed within the chamber and/or they may be arranged outside of the chamber such that they radiate heat through at least a portion of the chamber that is substantially transparent to the radiant energy (i.e. at least 90%, 95%, 99%, or any other appropriate transparency to the radiant energy). Correspondingly, a plurality of sensors may be configured to sense temperature, mass, optical properties or other appropriate operating parameter associated with the therapeutic composition disposed in different containers on different movers within the chamber. For example, noncontact temperature sensors such as pyrometers may be used to measure the temperature of containers including a therapeutic composition located on movers in different portions of a chamber. Other appropriate sensors may include, but are not limited to, optical cameras, refractometers, acoustic sensors, and/or any other appropriate sensor configured to sense one or more operating parameters associated with the therapeutic compositions. For example, a sensed temperature and/or mass of remaining therapeutic composition associated with the different movers may then be input to a processor which may then independently control each of the plurality of radiant heaters to independently maintain a temperature of the therapeutic composition in the containers on each mover within a desired temperature range which may either be the same or different for each mover depending on the embodiment and sensed operating parameters. Again, this may help to improve a uniformity of the processing of different batches of therapeutic composition that are processed by a lyophilization system as disclosed herein.

Due to the ability of the plurality of stators being able to electromagnetically control the movement of each mover independently, it may be possible to move movers through a system in a non-linear fashion. For example, if a particular batch of therapeutic composition supported on a mover needs additional time within a particular chamber, that particular mover may be moved out of a path of travel of the other movers within a chamber and/or other movers may be moved around the mover such that a dwell time of any individual mover may be increased or decreased based on one or more sensed parameters of the therapeutic composition. Appropriate parameters that may be sensed may include, but are not limited to, a temperature of a composition contained within one or more containers supported on a mover, a mass of therapeutic composition disposed within a container on a mover, reflectance, refraction, and/or any other appropriate operating parameter, as the disclosure is not limited in this fashion.

In view of the above, in some embodiments, the disclosed methods and systems herein may provide a serial flow-through system for lyophilizing containers containing aqueous based therapeutic compositions, where singular trays of vials containing therapeutic compositions are moved through the system without mechanical contact between each other or the system, in some embodiments. Further, in some embodiments, the movers that are electromagnetically levitated and moved through the lyophilization systems disclosed herein may correspond to systems such as the planar motors, which may be obtained from Planar Motors Inc. In such a construction, the stators may form the base structure of the system upon which the load lock chambers and processing chambers may be mounted, and the movers may convey racks of vials or other containers, of therapeutic compositions through the system. Additionally, as elaborated on herein, a lyophilization may also include a loading zone upstream from an inlet of the system and an unloading zone downstream from an outlet of the system. Thus, a desired therapeutic composition disposed in one or more containers supported on a mover may be easily provide to a first load lock to enable a mover to enter and be brought to the environmental condition of a conditioning chamber where the therapeutic composition may be brought to a desired processing condition. A second load lock may also be used to enable a mover to enter from the conditioning chamber and be brought to the environmental condition of a nucleation chamber prior to being moved into the nucleation chamber. A third load lock may be used to enable a mover to enter from the nucleation chamber and be brought to the environmental condition of a drying chamber. Depending on the embodiment, the drying chamber may be large enough such that it may contain many movers that slowly move through from one end to the other. Additionally, the drying chamber may be configured to provide a pressure for freeze drying between or equal to 10 Pascal and 0.1 Pascal (1.0 Pascal is $1/100,000^{th}$ of an atmosphere). Additionally, a temperature within the conditioning and/or drying chamber may be between or equal to a freezing temperature of water (0° C.) and about −80° C., and more preferably between about −30° C. and −80° C. The use of radiant heater zones within the drying chamber may also provide for independent heat control of the therapeutic compositions disposed in the containers on the separate movers within the drying chamber. To enable such a functionality, a plurality of sensors disposed within the drying chamber may be configured to sense one or more conditions of the therapeutic compositions, such as a temperature of the therapeutic composition, in the containers to enable feedback control of the radiant heater zones. Of course, after appropriately processing the therapeutic composition supported in one or more containers disposed on a mover, the mover may be passed through a fourth load lock to enable the mover to move from the drying chamber and be brought to the environmental condition of the outer atmosphere.

In view of the above, in some embodiments, the disclosed systems and methods may control the processing of therapeutic compounds with unprecedented precision while also offering decreased energy consumption and/or space usage. The disclosed systems and methods may also reduce the risk of out of specification product.

As used herein, the term therapeutic composition refers to a composition including an agent that may be administered to a subject to treat a disease, disorder, or other clinically recognized condition, or for prophylactic purposes, and has a clinically significant effect on the body of the subject to treat, prevent, and/or diagnose the disease, disorder, or condition. In some embodiments, therapeutic compositions can include, but are not limited to, any synthetic or naturally-occurring biologically active compound or composition of matter which, when administered to a subject (e.g., a human or nonhuman animal), induces a desired pharmacologic, immunogenic, and/or physiologic effect by local and/or systemic action. For example, useful or potentially useful within the context of certain embodiments are compounds or chemicals traditionally regarded as small molecule drugs, vaccines, and biopharmaceuticals. Certain such therapeutic compositions may include molecules such as organic compounds, proteins, peptides, monoclonal antibodies, exosomes, hormones, nucleic acids, gene constructs, etc., for use in therapeutic, diagnostic, and/or enhancement areas. Further, prior to lyophilization, a therapeutic composition may include a liquid, such as water or an organic solvent that the desired active compound or composition is suspended in. Accordingly, it should be understood that the therapeutic compositions described herein are not limited to any particular type of therapeutic composition.

Turning to the figures, specific non-limiting embodiments are described in further detail. It should be understood that the various systems, components, features, and methods described relative to these embodiments may be used either individually and/or in any desired combination as the disclosure is not limited to only the specific embodiments described herein.

FIG. 1 shows a lyophilization system 1 according to one illustrative embodiment. The lyophilization system 1 provides a serial flow-through system (e.g., a system allowing for units to be moved through the system sequentially) for lyophilizing vials containing aqueous based therapeutic compositions, where singular trays of vials holding therapeutic compounds are moved through the system on movers 20 without mechanical contact between each other or other portions of the system. Particularly, in the illustrated embodiment, movers 20 may include features that allow movers 20 to transport the vials without making mechanical contact with the remainder of lyophilization system 1. For example, the lyophilization system 1 may be formed of one or more stators, such as stators 2a, 2b, 2c, and 2d, configured to electromagnetically levitate and manipulate the movers 20. The stators 2s, 2b, 2c, 2d may form the base structure of the lyophilization system 1 and be assembled adjacent to each other on a supporting frame or surface (not shown) which may be formed from a metal (e.g., welded steel and/or modular aluminum) or other suitable framing. In some embodiments, the stators 2a, 2b, 2c, 2d may be associated with a substantially continuous surface that extends through the system with the stators disposed in, or located beneath, the substantially continuous surface such that the stators 2a, 2b, 2c, 2d are capable of electromagnetically interacting with the movers 20 to magnetically levitate and move the movers in a desired direction. Underneath the stators 2a, 2b, 2c, 2d and other depicted components, lyophilization system 1 may include process support equipment such as environmental control systems, vacuum pumps, control electronics, power supplies, and/or any other suitable mechanisms, depending on the application.

As discussed herein, a lyophilization system 1 may include features that allow for the movers 20 to be guided along a predetermined path through one or more processing chambers in a predetermined order (e.g., serial flow-through). For example, the stators 2a, 2b, 2c, 2d may be arranged on the lyophilization system 1 such that the movers 20 are guided from stator 2a to stator 2b to stator 2c to stator 2d, etc. Accordingly, in some embodiments, the stators 2a, 2b, 2c, 2d, may be positioned on the lyophilization system 1 such that the movers 20 are guided through a series of chambers.

For example, in some embodiments, lyophilization system 1 includes load lock chambers 10a, 10b, 10c, and 10d and process chambers 30a, 30b and 30c. In turn, the stators 2a, 2b, 2c, and 2d may be positioned such that the stators 2a, 2b, 2c, 2d may move the movers 20 through the load lock chambers 10a, 10b, 10c, and 10d, as well as chambers 30a, 30b, and 30c. Particularly, the stator 2a may electromagnetically levitate movers 20 initially located in a loading/unloading area 30L through a first load lock 10b and into a first process chamber 30a. Subsequently, the stator 2b may electromagnetically levitate the movers 20 through the first process chamber 30a, through the second load lock chamber 10c, and into the second process chamber 30b. In turn, the stator 2c may electromagnetically levitate the movers 20 through the second process chamber 30b, through the third load lock chamber 10d and into the third process chamber 30c. The stator 2d may then move the movers 20 through the third process chamber 30c (e.g., in the direction of the dashes arrows shown in FIG. 1). As shown in FIG. 1, the stators 2a, 2b, 2c, 2d may then serve to return the movers 20 to the loading/unloading area 30L through the fourth load lock chamber 10a. Of course while a particular arrangement and number of stators is shown in the figures and described above, it should be understood that any appropriate number of stators in any appropriate configuration may be used as the disclosure is not so limited.

The process chambers 30a, 30b, and 30c may be configured to perform any suitable function. For example, in some embodiments, one or more of the process chambers 30a, 30b, and 30c may take on the function of a nucleation chamber. In a nucleation process chamber, a composition may be processed such that its molecules crystalize. To facilitate the nucleation process, a pressure within the process chamber may be low enough to induce nucleation of solid crystals of the composition in the nucleation chamber. Alternatively or in addition, in some embodiments, one or more of the process chambers 30a, 30b, and 30c may take on the function of a drying chamber. The drying chamber may apply an appropriate combination of temperature and reduced pressure as noted above in order to dry the composition in a frozen state such that the physical structure and/or the stability of the composition is maintained. Alternatively or in addition, in some embodiments, one or more of the process chambers 30a, 30b, and 30c may take on the function of a conditioning chamber. The conditioning chamber may serve to bring the composition within an appropriate operating parameter range for additional processing. For example, in some instances, the conditioning chamber may serve to bring the composition to a predetermined conditioning temperature such that the composition may then be crystallized and dried. Of course, any suitable parameter of the composition may be conditioned in a conditioning chamber, depending on the application.

In some embodiments, the lyophilization system 1 may include an outer structure 3 (e.g., as shown in phantom in FIG. 1), such as an exterior housing, configured to isolate the internal volume of the system, such as the one or more processing chambers or load lock chambers, from the surrounding environment. Additionally, in some instances, the outer structure may also be appropriately sealed and constructed to maintain a desired vacuum relative to the surrounding atmospheric pressure depending on the particular process being performed in that portion of the system. The outer structure 3 may be formed of any suitable material, including titanium, nickel alloys, stainless steel, carbon steel, aluminum, hastelloy, plastics, combinations of the foregoing, and/or any other appropriate material as the disclosure is not so limited.

In some embodiments, a lyophilization system 1 may include a loading/unloading zone 30L at one end that may be serviced by a robotic manipulator 40, an operator, and/or any other appropriate method. The robotic manipulator 40 may be configured to load and/or unload one or more containers (e.g., vials) onto the movers 20, for example, from an input and output conveyor supply system (not shown), a service cart such as a mobile robot, or a manually loaded pickup location. The robotic manipulator 40 may include an arm and an end effector that may be operated to load and unload one or more containers onto and off of the movers 20. Thus, the robotic manipulator 40 may be used to control the flow of containers containing a therapeutic composition into and out of the lyophilization system. However, other loading and unloading methods, including manual loading and unloading of the movers, may also be used as the disclosure is not limited in this fashion. Additionally, instances in which movers with a load of containers disposed thereon are loaded into and removed from the system are so contemplated.

Depending on the embodiment, a system may also include one or more processors 32. The one or more processors may be configured to: control operation of the stators 2a-2d to control movement of the one or more movers through the system; control processing parameters within the one or more chambers 30a-30c; operation of the robotic manipulator 40; the one or more load locks 10a-10d; combinations of the foregoing; and/or the operation of any other appropriate component of a lyophilization system. Additionally, the one or more processors may be associated with corresponding non-transitory processor readable memory that includes instructions that when executed cause the lyophilization system to operate according to any of the methods described herein.

Figure 3:
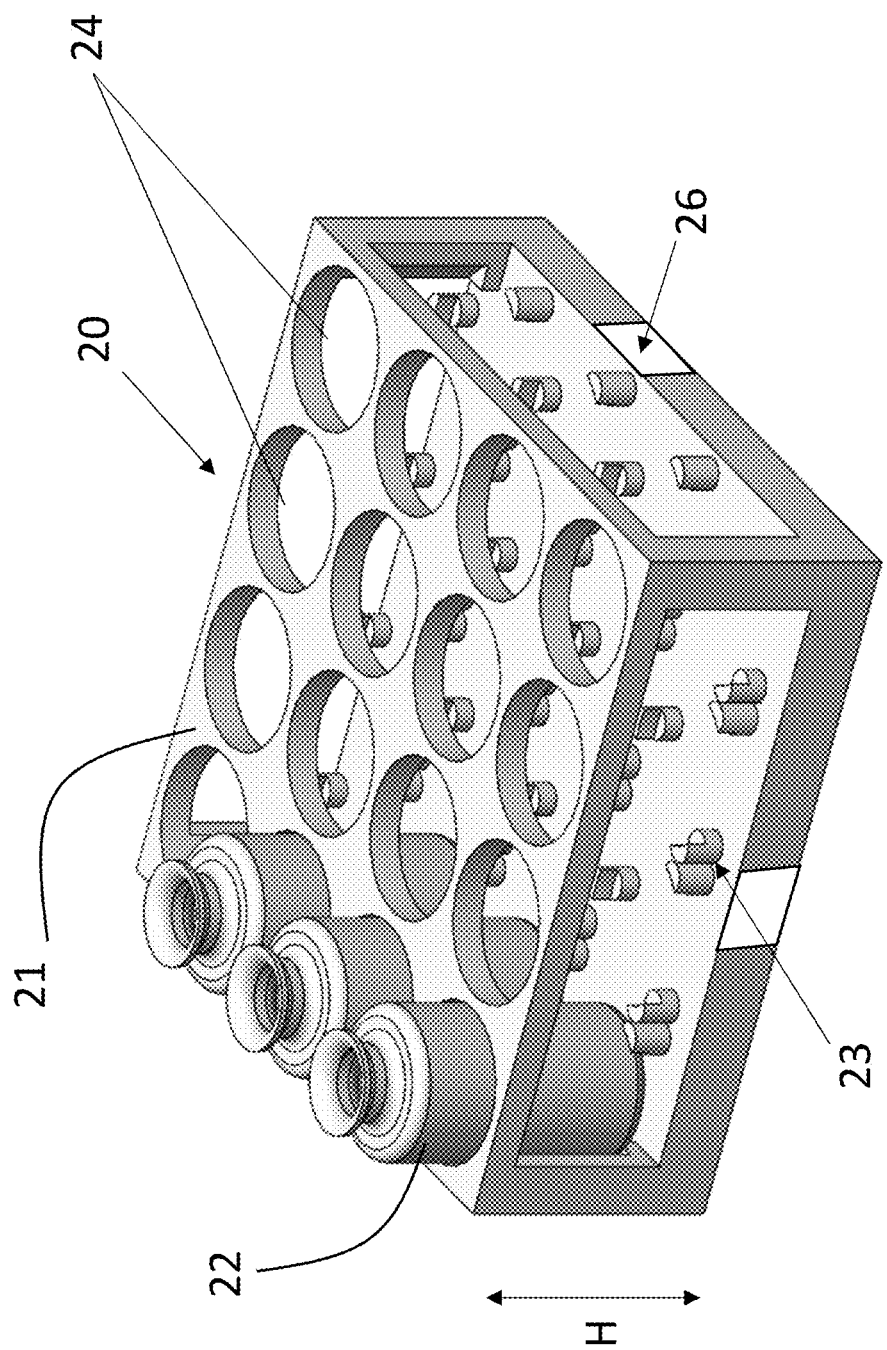
FIG. 3 is an isometric view of a vial support tray and vials according to one embodiment.

As noted above, the stators 2a, 2b, 2c, 2d of the system may be controlled to manipulate an electromagnetic field applied to the one or more movers supported vertically above the one or more stators relative to a direction of gravity as the movers are moved through the system. FIG. 3 shows a mover 20 according to one exemplary embodiment. The bottom portion of the mover 20, and in some embodiments and the interior bottom portion of the mover, may include one or more magnets 26, which may interact with electromagnetic fields emitted by the coils disposed within the stators 2a, 2b, 2c, 2d to enable the non-contact levitation and motion described herein. In some embodiments, the coils disposed in stators 2a, 2b, 2c, 2d may be computer or processor controlled.

In some embodiments, a top portion of the mover may include a frame structure 21 having a plurality of apertures 24 sized and shaped to receive a corresponding plurality of containers 22 (e.g., vials). The frame 21 may be disposed at a height H away from a base of the mover 20 such that the containers 22 remain more stable as the mover 20 is moved. Particularly, the height H may be set such that the frame structure 21 of the mover 20 may be set such that a centroid of each of the containers 22 is located vertically below the frame structure 21. Alternatively or in addition, the mover 20 may include supports 23 configured to engage with a bottom surface of a corresponding container to further stabilize the containers 22 within the mover 20. In some embodiments, the one or more supports associated with an individual container may include cut out portions that are sized and shaped to engage with an edge portion of the associated container 22. In the depicted embodiment, a plurality of supports engage separate portions of a bottom edge of a container to maintain a desired position and orientation of the container within the mover.

Figure 2:
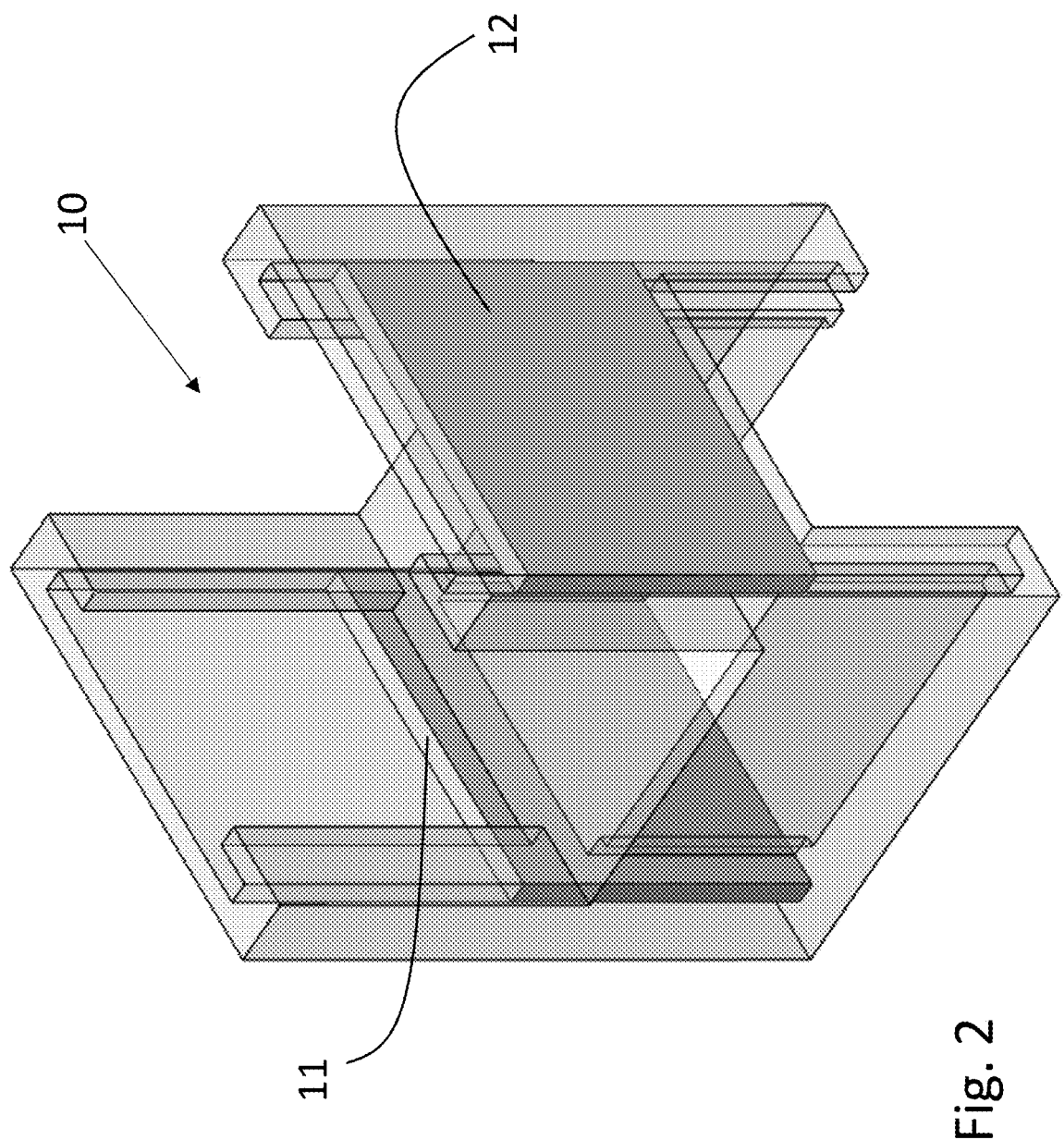
FIG. 2 is an isometric view of a load lock according to one embodiment.

FIG. 2 shows a load lock 10 according to one illustrative embodiment. Load lock 10 may serve to isolate the contents of the containers held on the one or more movers 20. Particularly, the load lock 10 may bring the contents of the containers held on the one or more movers 20 to the environmental condition (e.g., pressure, temperature, etc.) of one or more process chambers 30a, 30b, and 30c. Load lock 10 may be capable of opening a first door 11 of the load lock 10 to allow one or more movers 20 to enter the load lock 10. The first door 11 of the load lock 10 may then close, isolating the one or more movers within the environment of the load lock 10. The contents of the one or more movers disposed within the load lock 10 may be brought to the desired environmental condition. Then, a second door 12 of the load lock may open, allowing the one or more movers 20 to proceed into the processing chamber. In some embodiments, the load lock 10 may include a space sized and shaped to accommodate one of the one or more movers 20 such that the one or more movers proceed into the processing chamber sequentially. Accordingly, in some embodiments, as the second door 12 opens one of the one or more movers 20 may be received in the process chamber without all other movers 20 having to synchronously move. The second door may then be closed, allowing another mover or set of movers to enter the load lock 10.

As shown in FIG. 2, the first and second doors 11, 12 may be gate valves associated with one or more actuators that control the selective opening and closing of the first and second doors 11, 12. However, other types of sealable doors, such as doors whose opening and closing can be controlled using one or more associated actuators, may be used. For example, the first and/or second doors 11, 12 may be rotating doors, biased folding doors, piston-actuated doors, or any other suitable type of door and/or type of actuator. Of course other types of doors may be employed, depending on the application.

Turning again to FIG. 1, in some embodiments, a lyophilization system includes a first process chamber 30a configured as a conditioning chamber. The first process chamber 30a may include processor-controlled valves (e.g., controlled by the processor 32) may be used to enable gas to enter or exit the chamber in accordance with the environment in the chamber, which may be sensed by a sensor such as a temperature, pressure, humidity, and/or any other appropriate type of sensor. In concert, flow from a gas source and/or to a vacuum source such as a pump, may also be controlled by an associated processor (e.g., the processor 32). In the cooling conditioning chamber, cold gas may flow across the movers which may enhance a cooling rate of the therapeutic composition included in the one or more containers supported by the movers. However, in some embodiments, the flow of cold gas within the chamber across the movers may be may be controlled so as to maintain a desired trajectory of the movers and minimize vibration of the containers being carried by the movers to avoid improper (i.e., premature unstructured) nucleation. In either case, the environmental conditions and dwell time in the first process chamber 30*a* (e.g., the conditioning chamber) may be appropriate to cool the containers of therapeutic compound to a desired processing temperature for the subsequent nucleation process.

A second load lock 10*c* may be disposed between the first process chamber 30*a* (e.g., the conditioning chamber) and a second process chamber 30*b* (e.g., a nucleation chamber), and the second load lock 10*c* may operate in a manner similar to that described above. Thus, the second load lock chamber 10*c* may allow a mover to enter from the first process chamber 30*a* (e.g., the conditioning chamber) and be brought to an environmental condition of the second process chamber 30*b* (e.g., the nucleation chamber). Accordingly, the load lock 10*c* environment may be brought to the conditioning chamber environment state and then its first door 11 may open allowing one or more movers 20 with one or more containers including the therapeutic composition that had been conditioned in the first process chamber 30*a* to enter the load lock 10*c*. Then, the load lock 10 *c* may operate (e.g., as described herein) to modify the environment surrounding the one or more movers 20 within the load lock 10*c* to the environment of the second process chamber 30*b*.

Nucleation may occur within a process chamber (e.g., process chamber 30*b*) in any suitable manner. Some suitable manners of nucleation include, but are not limited to, rapid temperature drop, shock induced nucleation, pressure induced nucleation, and/or suitable in any other suitable manner. In some embodiments, such as embodiments performing shock induced nucleation, the movers may be actuated in a way to induce nucleation mechanically. In some embodiments, nucleation may be induced to affect crystal growth for controlled crystal size for heat and mass transfer during drying.

Of course, embodiments in which the conditioning chamber and nucleation chamber are combined into a single chamber are also contemplated as the disclosure is not limited in this fashion. Nucleation of crystallization in the therapeutic compound disposed in the containers may be initiated in a variety of ways including, but not limited to, using the movers to shake the solution, inducing stress, reducing pressure within a chamber rapidly, reducing temperature within a chamber rapidly, ultrasonically induced nucleation, laser-induced nucleation, and/or any other appropriate method for inducing nucleation as these examples are not meant to be limiting.

A third load lock 10*d* similar to those described herein may also be disposed between the nucleation chamber and the drying chamber. The third load lock 10*d* may enable one or more movers 20 to enter from the nucleation chamber and be brought to the environmental condition of the drying chamber. As described herein, the load lock 10*d* environment may be brought to the nucleation chamber environment state and then its first door 11 may be opened allowing one or more movers 20 with its containers including a therapeutic composition that had been conditioned to enter the load lock 10*c* and the first door of the load lock 10*d* may then close. The environment in the load lock 10*d* may then be brought to that of the third process chamber 30*c* (e.g., a drying chamber).

The conditioning and nucleation steps may take on the order of minutes, while the drying process may be on the order of hours. Thus, the drying chamber 30*c* may be much larger than the other chambers to permit a dwell time of each mover within the drying chamber to be correspondingly longer. In some instances, this may correspond to a large chamber where a path of the individual movers may zig zag back and forth across a width of the chamber as the movers move from an inlet to an outlet of the drying chamber, as shown by the dashed arrows in FIG. 1. In some embodiments, this may permit the footprint of a system to be minimized while maximizing control of each mover's payload's drying process. Of course, while a particular drying chamber and travel path of the movers through the drying chamber is depicted in the figures, it should be understood that the current disclosure is not limited to any particular size, shape, or path as the disclosure is not limited in this fashion.

In some embodiments, a drying chamber may have a pressure that is between or equal to 0.1 to 100.0 Pascals (one Newton per square millimeter) and more preferably between 1.0 and 3.0 Pascals. Of course, higher pressures may be employed, but in some embodiments, employing a higher pressure may result in an increased drying time. Additionally, a temperature of the thin atmosphere in the drying chamber may be between about 50° C. and −80° C., and preferably between 20° C. and −20° C. but this may be dependent on the therapeutic composition and its crystallography.

In the embodiments discussed herein, the movers 20 may be loaded and unloaded at one end of the system and the movers 20 may move back and forth in a zigzag pattern (e.g., as shown in dashed arrows in FIG. 1) within the drying chamber. However, in other embodiments, it may be preferred to have a longer layout of the system such that more systems can be placed side by side near each other, with easy access to the side walls of the systems for monitoring or repair. In addition, the movers may be loaded at one end of the system and then unloaded at the other end of the system in accordance with overall flow through a factory for the containers. Accordingly, it should be understood that the methods and systems disclosed herein are not limited to any particular layout and/or path of the movers through a system as the disclosure is not so limited. In any of these layouts, a vacuum system may be sized accordingly to keep the chamber at the proper pressure to accommodate any leakage that is present in the system.

As noted previously, in some embodiments, may be desirable to control a temperature of a therapeutic compound contained within one or more containers disposed on a mover as the mover travels through a system. Accordingly, in some embodiments, a lyophilization system may include one or more heaters 25, which may be formed as part of the third process chamber 30*c* (e.g., the drying chamber). The heaters 25 may be operatively coupled with one or more associated power supplies, not depicted, and one or more processors, such as processor 32, to control the amount of energy that the heaters radiate to the mover(s) beneath them. The walls of the chamber may also be appropriately insulated or temperature controlled to further control the environment inside the drying chamber.

In some embodiments, the plurality of heaters may be a plurality of radiant heaters disposed above a path of travel of the movers through a drying chamber 30c. A plurality of associated sensors may be configured to detect the state of drying of the drug within the vial. This may allow each heater's output to be adjusted by an associated processor, such as the depicted processor 32, to control a desired drying process for each movers' load of containers. Sensing can be direct optical observation of the product in the vial through the open top of the vial, or measurement of mass of the product in the vial by observing the position of the vial on the vial holder as the vial holder changes shape due to constantly decreasing mass of the vial and product as ice sublimates. Either static deflection or dynamic deflection of a supporting structural member supporting an associated container may be sensed to indirectly determine a mass contained in a given container. Alternatively, the mass may be determined using an observed change in natural frequency of the containers supported on a mover. Appropriate types of sensors may include, but are not limited to, optical (laser distance, moire, structured light) non-contact distance measuring sensors that can operate in a vacuum. The measurement of the deflection of a known structural member that supports an object, in order to determine the target's mass is a well-known method of mass measurement. In this application, a mover's ability to position each vial's support structure under a measurement system is unique in enabling the mass of each vial and its contents to be determined at multiple locations within the drying chamber and hence may provide feedback to the system controller to independently control the radiant heaters in conjunction with also measuring optically the therapeutic compound's temperatures within a given container or set of containers.

Once drying is complete, a fourth load lock 10a disposed between the external environment and the drying chamber 30c may enable the movers 20 to exit the drying chamber and be brought to the environmental condition of the external environment. The doors and chamber environment state may be operated in a manner similar to that described above for the other load locks.

In some embodiments, it may be desirable for the containers to enter a lyophilization system without caps on the containers so sensors may look down through the tops of the vials to directly observe the state of the therapeutic composition in each vial as it is being processed from the conditioning to the nucleation to the drying stage. In this scenario, empty clean containers would be loaded onto the movers and a therapeutic composition may be dispensed to a desired level in each container before entering the conditioning region. As such, there would be no cap on the container. However, at the end of the process while still in the vacuum zone of the drying region, it may be desirable to have a capping station to place a cap onto each vial, and then when the vials were returned to atmospheric conditions, atmospheric pressure would further press onto the cap and maintain a hermetic seal to preserve the product inside until it is ready to be reconstituted and injected into a patient.

As noted previously, in some embodiments, one or more processors 32 with associated non-transitory processor readable medium may be included in a lyophilization system 1 as depicted in FIG. 1. Depending on the particular embodiment, the one or more processors may be operatively coupled with the various controlled components and chambers described above relative to the lyophilization system including, but not limited to, the individual stators 2a, 2b, 2c, 2d, the load lock chambers 10a, 10b, 10c, 10d, the radiant heaters 25, the various temperature and atmospheric controls within each chamber, the various disclosed sensors, and/or any other appropriate component of a lyophilization system as the disclosure is not so limited. Accordingly, the one or more processors may be configured to operate these various components using any of the methods disclosed herein. For example, processor readable instructions may be stored in the non-transitory processor readable medium such that when they are executed by the one or more processors the lyophilization system performs any of the methods and/or operations described herein.

Figure 4:
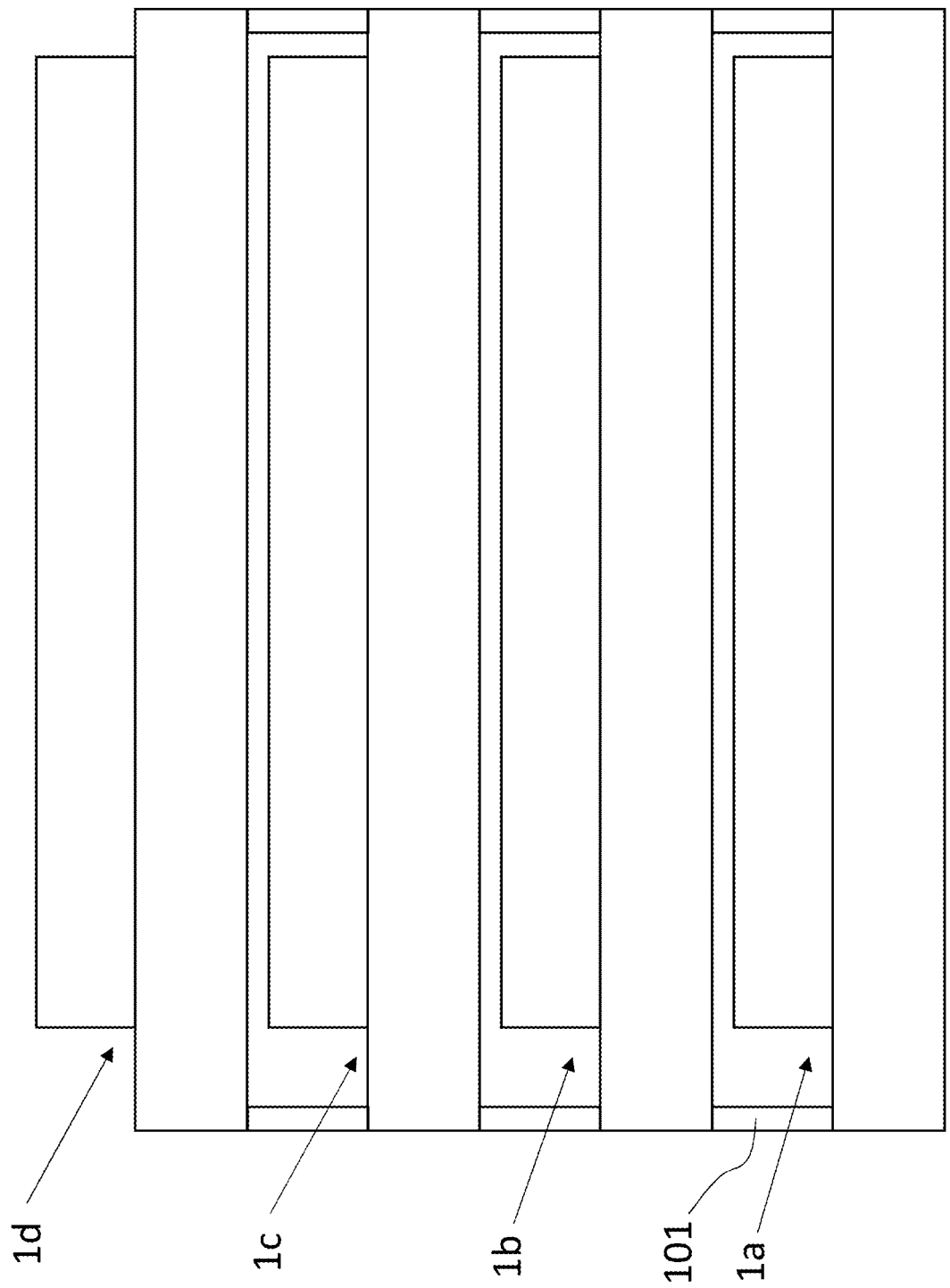
FIG. 4 is a schematic showing how systems can be stacked vertically to increase yield per floorspace according to one embodiment.

FIG. 4 shows one embodiment of how multiple lyophilization systems may be stacked vertically. For example, an overall system may include multiple lyophilization systems such as systems 1a, 1b, 1c, and 1d, as depicted in FIG. 4, where each of the systems is similar to the lyophilization system described herein (e.g., relative to FIG. 1). In the depicted embodiment, the lyophilization systems are stacked vertically on top of one another using a plurality of support structures 101 extending between adjacent lyophilization systems to provide vertical and horizontal support between them and an underlying supporting surface, such as a factory floor. Such an arrangement may help to minimize the floorspace used to produce a desired output and may be made possible by the low profile of the disclosed systems. However, instances in which systems are not stacked vertically on top of one another also contemplated as the disclosure is not so limited.

Figure 5:
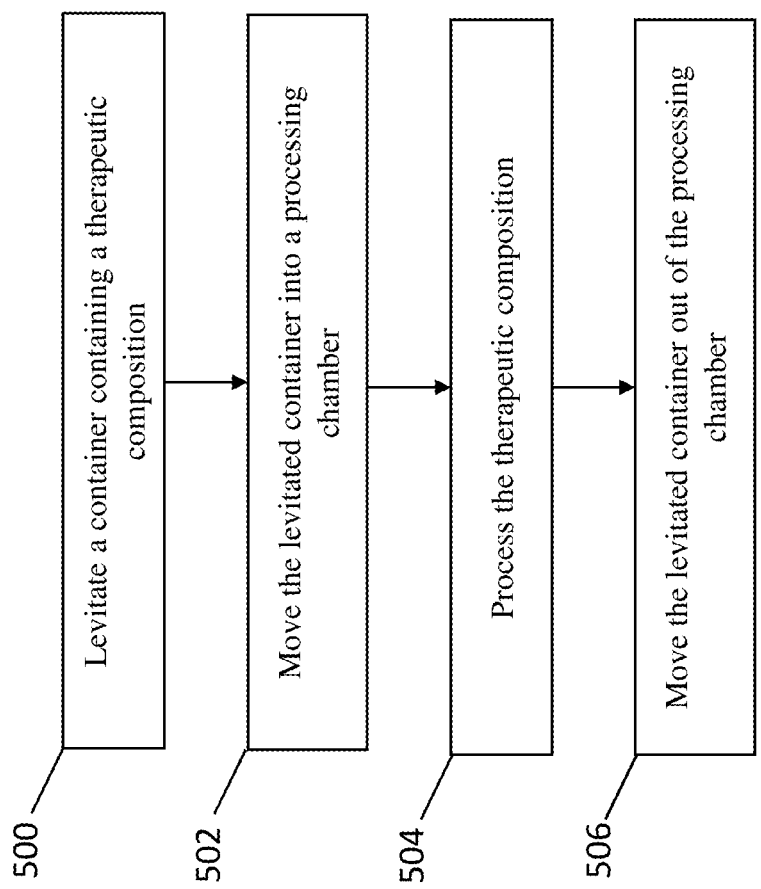
FIG. 5 is a flowchart showing a method of lyophilizing a therapeutic composition.

The present disclosure may also be embodied as a method of lyophilizing a therapeutic composition. For example, FIG. 5 is a flowchart depicting a method of lyophilizing a therapeutic composition. At step 500, a mover having a container holding a therapeutic compound therein may be electromagnetically levitated by one or more stators of a lyophilization system. At step 502, the stators may then guide the mover, which holds the container, into a processing chamber. At step 504, the therapeutic composition within the container may be processed within the process chamber. Subsequently, at step 506, the stators may then move the container holding the processed therapeutic compound out of the process chamber by electromagnetically levitating the mover.

The above-described embodiments of the technology described herein can be implemented in any of numerous ways. For example, the embodiments may be implemented using hardware, software or a combination thereof. When implemented in software, the software code can be executed on any suitable processor or collection of processors, whether provided in a single computing device or distributed among multiple computing devices. Such processors may be implemented as integrated circuits, with one or more processors in an integrated circuit component, including commercially available integrated circuit components known in the art by names such as CPU chips, GPU chips, microprocessor, microcontroller, or co-processor. Alternatively, a processor may be implemented in custom circuitry, such as an ASIC, or semicustom circuitry resulting from configuring a programmable logic device. As yet a further alternative, a processor may be a portion of a larger circuit or semiconductor device, whether commercially available, semi-custom or custom. As a specific example, some commercially available microprocessors have multiple cores such that one or a subset of those cores may constitute a processor. Though, a processor may be implemented using circuitry in any suitable format.

Further, it should be appreciated that a computing device may be embodied in any of a number of forms, such as an integrated computing device, a rack-mounted computer, a desktop computer, a laptop computer, or a tablet computer. Additionally, a computing device may be embedded in a device not generally regarded as a computing device but with suitable processing capabilities, including a Personal Digital Assistant (PDA), a smart phone, tablet, or any other suitable portable or fixed electronic device.

Also, a computing device may have one or more input and output devices. These devices can be used, among other things, to present a user interface. Examples of output devices that can be used to provide a user interface include display screens for visual presentation of output and speakers or other sound generating devices for audible presentation of output. Examples of input devices that can be used for a user interface include keyboards, individual buttons, and pointing devices, such as mice, touch pads, and digitizing tablets. As another example, a computing device may receive input information through speech recognition or in other audible format.

Such computing devices may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the embodiments described herein may be embodied as a processor readable storage medium (or multiple processor readable media) (e.g., a computer memory, one or more floppy discs, compact discs (CD), optical discs, digital video disks (DVD), magnetic tapes, flash memories, RAM, ROM, EEPROM, circuit configurations in Field Programmable Gate Arrays or other semiconductor devices, or other tangible computer storage medium) encoded with one or more programs that, when executed on one or more computers or other processors, perform methods that implement the various embodiments discussed above. As is apparent from the foregoing examples, a processor readable storage medium may retain information for a sufficient time to provide processor-executable instructions in a non-transitory form. Such a processor readable storage medium or media can be transportable, such that the program or programs stored thereon can be loaded onto one or more different computing devices or other processors to implement various aspects of the present disclosure as discussed above. As used herein, the term "processor-readable storage medium" encompasses only a non-transitory computer-readable medium that can be considered to be a manufacture (i.e., article of manufacture) or a machine. Alternatively or additionally, the disclosure may be embodied as a processor readable medium other than a computer-readable storage medium, such as a propagating signal.

The terms "program" or "software" are used herein in a generic sense to refer to any type of computer code or set of processor-executable instructions that can be employed to program a computing device or other processor to implement various aspects of the present disclosure as discussed above. Additionally, it should be appreciated that according to one aspect of this embodiment, one or more computer programs that when executed perform methods of the present disclosure need not reside on a single computing device or processor, but may be distributed in a modular fashion amongst a number of different computers or processors to implement various aspects of the present disclosure.

Processor-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

The embodiments described herein may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Further, some actions are described as taken by a "user." It should be appreciated that a "user" need not be a single individual, and that in some embodiments, actions attributable to a "user" may be performed by a team of individuals and/or an individual in combination with computer-assisted tools or other mechanisms.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. A system for lyophilization of pharmaceutical products comprising:
   at least one mover configured to support one or more containers containing a therapeutic composition;
   an inlet of the system for receiving the at least one mover;
   an outlet of the system for outputting the at least one mover from the system;
   a plurality of chambers disposed between the inlet and outlet, wherein the plurality of chambers includes at least a first chamber configured to perform a nucleation operation on the therapeutic composition and a second chamber disposed downstream of the first chamber configured to perform a vacuum drying operation on the therapeutic composition; and
   a plurality of stators configured to electromagnetically levitate and move the at least one mover from the inlet, through the plurality of chambers, and to the outlet.

2. The system of claim 1, wherein the plurality of stators are disposed in a substantially continuous surface extending from the inlet through the plurality of chambers to the outlet, and wherein the at least one mover is disposed on the substantially continuous surface.

3. The system of claim 1, further including a third chamber disposed between the inlet and the first chamber, wherein the third chamber is configured to perform a conditioning operation on the therapeutic composition.

4. The system of claim 1, wherein the at least one mover is a plurality of movers, and wherein the plurality of stators is configured to independently control motion of each mover of the plurality of movers.

5. The system of claim 1, further comprising a plurality of load lock chambers configured to isolate an atmosphere within each chamber of the plurality of chambers from an external environment and adjacent chambers.

6. The system of claim 1, further comprising a plurality of radiant heaters configured to heat the one or more containers supported on the at least one mover while the at least one mover is disposed in the second chamber, and wherein the plurality of radiant heaters are independently controllable and are directed towards separate portions of the second chamber.

7. The system of claim 6, further comprising a plurality of sensors configured to sense a temperature of the one or more containers of the therapeutic composition supported on the at least one mover in the separate portions of the second chamber.

8. The system of claim 1, further including a processor configured to perform the steps of:
controlling the plurality of stators to move the at least one mover from the inlet into the first chamber;
controlling operation of the first chamber and the at least one mover to perform the nucleation operation;
controlling the plurality of stators to move the at least one mover from the first chamber to the second chamber;
controlling operation of the second chamber and the at least one mover to perform the vacuum drying operation; and
controlling the plurality of stators to move the at least one mover from the second chamber to the outlet.

9. A method of lyophilizing a therapeutic composition, the method comprising:
electromagnetically levitating at least one container including the therapeutic composition;
electromagnetically moving the at least one container into a first chamber;
performing a nucleation operation on the therapeutic composition in the first chamber;
electromagnetically moving the at least one container from the first chamber to a second chamber;
performing a vacuum drying operation on the therapeutic composition in the second chamber; and
electromagnetically moving the at least one container out of the second chamber.

10. The method of claim 9, further including super cooling a liquid the therapeutic composition is disposed in before electromagnetically moving the at least one container into the first chamber.

11. The method of claim 9, further comprising controlling a temperature of the at least one container and the therapeutic compositions contained therein using radiant heating during the vacuum drying operation.

12. The radiant heating of claim 11, wherein the radiant heating is provided using individual radiant heaters that are independently controlled.

13. The method of claim 11, wherein the at least one container is a plurality of groups of containers supported on a plurality of movers disposed in the second chamber, and wherein a temperature of separate groups of the plurality of groups of containers disposed on separate movers of the plurality of movers are independently controlled using the radiant heating.

14. The method of claim 9, wherein electromagnetically moving the at least one container through the first chamber, into the second chamber, and out of the second chamber includes electromagnetically moving the at least one container over a substantially continuous surface extending between an inlet and an outlet.

15. The method of claim 9, further comprising controlling and isolating an atmosphere within each chamber from an external atmosphere and adjacent chambers.

16. A system for lyophilization of pharmaceutical products comprising:
at least one mover configured to support one or more containers containing a therapeutic composition;
an inlet of the system for receiving the at least one mover;
an outlet of the system for outputting the at least one mover from the system;
at least one load lock chamber disposed between the inlet and outlet;
at least one process chamber disposed downstream of the load lock chamber;
a plurality of stators configured to electromagnetically levitate and move the at least one mover from the inlet, through the at least one load lock chamber and the at least one process chamber to the outlet;
at least one processor configured to control the stators, the at least one load lock chamber, and the at least one process chamber.

17. The system of claim 16, wherein the at least one processor is configured to perform the steps of:
setting an environment of the at least one load lock chamber to an environment of the inlet;
opening a first door of the at least one load lock chamber;
controlling the plurality of stators to electromagnetically levitate and move the at least one mover into the at least one load lock chamber through the first door;
closing the first door of the at least one load lock chamber;
setting the environment of the at least one load lock chamber to an environment of the at least one process chamber;
opening a second door of the load lock chamber;
controlling the plurality of stators to electromagnetically levitate and move the at least one mover into the at least one process chamber through the second door;
closing the second door.

18. The system of claim 17, wherein the at least one processor is further configured to perform the steps of:
controlling the at least one process chamber to process the therapeutic composition;
controlling the plurality of stators to electromagnetically levitate and move the at least one mover from the at least one process chamber to the outlet.

19. The system of claim 16, wherein the plurality of stators are disposed in a substantially continuous surface extending from the inlet through the at least one load lock chamber and the at least one process chamber to the outlet, and wherein the at least one mover is disposed on the substantially continuous surface.

20. The system of claim 16, wherein the at least one mover is a plurality of movers, and wherein the plurality of stators is configured to independently control motion of each mover of the plurality of movers.

* * * * *